United States Patent

Schlesinger et al.

[11] 4,091,025
[45] May 23, 1978

[54] PROCESS FOR THE MANUFACTURE OF NITROAMINOPYRIDINES

[75] Inventors: Ulrich Schlesinger, Maulburg, Baden, Germany; Visvanathan Ramanathan, Basel, Switzerland

[73] Assignee: Ciba-Geigy AG, Basel, Switzerland

[21] Appl. No.: 730,403

[22] Filed: Oct. 7, 1976

[30] Foreign Application Priority Data

Oct. 24, 1975 Switzerland .................. 13798/75
Oct. 27, 1975 Switzerland .................. 13881/75

[51] Int. Cl.$^2$ .................................. C07D 213/61
[52] U.S. Cl. .................... 260/294.8 F; 424/246; 424/248.56; 424/250; 424/263; 260/154; 260/156; 260/293.69; 260/294.8 D; 260/296 R; 544/60; 544/124; 544/360; 544/364; 544/357
[58] Field of Search ......... 260/296 R, 294.9, 294.8 F, 260/268 H, 293.69; 544/124

[56] References Cited

U.S. PATENT DOCUMENTS

| | | | |
|---|---|---|---|
| 3,862,157 | 1/1975 | Wiskott | 260/293.69 |
| 3,907,769 | 9/1975 | Dehnert et al. | 260/156 |
| 3,998,802 | 12/1976 | Dehnert et al. | 260/156 |
| 4,000,146 | 12/1976 | Gerber | 260/296 R |

OTHER PUBLICATIONS

Klingsberg, Pyridine and Its Derivatives, Part Three, pp. 60–61, 206 & 232 to 233, Interscience Publishers (1962).

Primary Examiner—John D. Randolph
Attorney, Agent, or Firm—Edward McC. Roberts; Prabodh I. Almaula

[57] ABSTRACT

A process for the manufacture of 2,4,6-triamino-5-nitropyridines of the general formula

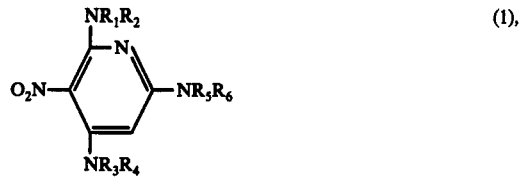

wherein each of $R_1$, $R_2$, $R_3$, $R_4$, $R_5$ and $R_6$ represents a hydrogen atom, a substituted or unsubstituted aryl, aralkyl or cycloalkyl group or an aliphatic group, and $R_1$ and $R_2$, $R_3$ and $R_4$, and $R_5$ and $R_6$ together can form a ring which contains the amino-nitrogen, which process comprises (a) aminating a 2-halogeno-3-cyano-4,6-diaminopyridine, preferably 2-bromo-3-cyano-4,6-diaminopyridine either to give the triaminopyridine of the formula

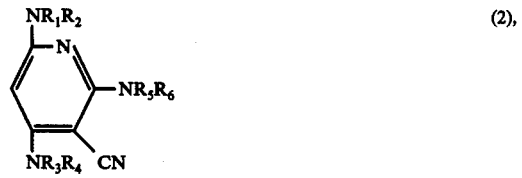

wherein $R_1$, $R_2$, $R_3$, $R_4$, $R_5$ and $R_6$ are as defined above, and then treating this product initially with nitrating agents and subsequently saponifying the cyano group until decarboxylation has been effected, or (b) treating it with nitrating agents and aminating the 2-halogen atom, namely the 2-bromine atom, in the resultant 5-nitro product and subsequently saponifying the cyano group until decarboxylation has been effected.

The nitropyridines obtained are valuable coupling components for the synthesis of azo dyestuffs.

8 Claims, No Drawings

PROCESS FOR THE MANUFACTURE OF NITROAMINOPYRIDINES

The invention provides a novel process for the manufacture of 2,4,6-triamino-5-nitro-pyridines of the general formula

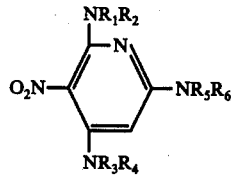

(1), wherein each of $R_1$, $R_2$, $R_3$, $R_4$, $R_5$ and $R_6$ represents a hydrogen atom, a substituted or unsubstituted aryl, aralkyl or cycloalkyl group or an aliphatic group, and $R_1$ and $R_2$, $R_3$ and $R_4$, and $R_5$ and $R_6$ together can form a ring which contains the amino-nitrogen, which process comprises (a) aminating a 2-halogeno-3-cyano-4,6-diaminopyridine, preferably 2-bromo-3-cyano-4,6-diaminopyridine, either to give the triaminopyridine of the formula

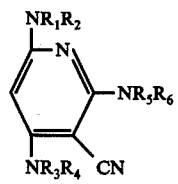

(2), wherein $R_1$, $R_2$, $R_3$, $R_4$, $R_5$ and $R_6$ are as defined above, and then treating this product with nitrating agents and subsequently saponifying the cyano group until decarboxylation has taken place, or (b) treating it with nitrating agents and aminating the 2-halogen atom, namely the 2-bromine atom, in the resultant 5-nitro product, and subsequently saponifying the cyano group until decarboxylation has been effected.

The nitration is advantageously carried out with the nitrosulphuric acid customarily used in the art, i.e. in a mixture of 1 to 50 parts of nitric acid and 50 to 99 parts of sulphuric acid, at temperatures of −20° to +60° C, preferably at temperatures of 0° to 25° C.

The amination is the reaction of the labile halogen atom with primary or secondary amines or ammonia. Suitable primary or secondary amines are: methylamine, ethylamine, dimethylamine, diethylamine, dipropylamine, di-n-butylamine, N-methyl-N-butylamine, N-(2-hydroxyethyl)amine, N-(2-chloroethyl)amine, N-(2-methoxyethyl)amine, N-(2-cyanoethyl)amine, N,N-di-(2-hydroxyethyl)amine, N,N-di-(2-chloroethyl)amine, N,N-di-(2-methoxyethyl)amine, N,N-di-(2-cyanoethyl)amine, N-2-cyanoethyl-N-ethylamine, N-2-cyanoethyl-N-2-hydroxyethylamine, N-2-lower alkoxy (for example $C_1$–$C_4$-alkoxy)-N-lower alkyl (for example $C_1$–$C_4$-alkyl, in particular methyl)-amine, N-methoxyethyl-N-cyanoethyl amine, N-methyl-N-ethanolamine, N-2-methylthioethylamine, N-2-methylsulphonylethylamine, γ-methoxypropylamine, γ-cyanopropylamine, γ-carboxylpropylamine, γ-sulphopropylamine, N-hydroxy-ethyl-N-cyclohexylamine, 3-hydroxy-1,1-dimethylpropylamine, benzylamine, o-, m-, p-nitrobenzylamine, o-, m-, p-methylbenzylamine, o-, m-, p-methoxybenzylamine, phenylethylamine, cyclohexylamine, methylcyclohexylamine, 2,2,5-trimethylcyclohexylamine, dicyclohexylamine, tetramethylenesulphonyl-3-amine, N-pyrrolidine, N-piperidine, N-methylpiperidine, N-morpholine, N-4-sulphopiperidine(N-thiomorpholine)

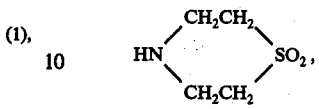

(for example methyl-piperazine), N-(N'-lower alkylcarbonyl, for example acetyl)-piperazine, N-(N'-hydroxyethyl)-piperazine, phenylamine, o-, p-, m-chlorophenylamine, 3,6-dichlorophenylamine, o-, m-, p-bromophenylamine, o-, p-fluorophenylamine, m-trifluoromethylphenylamine, m-, p-nitrophenylamine, o-, m-, p-methylphenylamine, o-, m-, p-lower alkoxy phenylamine, such as o-, m-, p-methoxyphenylamine, m-, p-carboxyphenylamine, m-, p-carboxamidophenylamine, m-, p-acetamidophenylamine, p-, m-aminosulphonylphenylamine, m-(bis-(hydroxyethylamino)-sulphonylphenylamine, methylsulphonylphenylamine, p-(2-hydroxyethyl)-sulphonylphenylamine, N-cyclohexyl-N-phenylamine, N-methyl-N-phenylamine, N-phenyl-N-2-hydroxyethylamine, N-phenyl-N-2-cyanoethylamine, N-p-chlorophenyl-N-2-hydroxyethylamine, p-phenoxyphenylamine, p-(p'-chlorophenoxy)-phenylamine, p'-methylphenoxyphenylamine, m-chloro-o-phenyloxyphenylamine, p-benzylphenylamine, p-acetamidophenylamine and p-propionylamidophenylamine, thiazolyl-2-amine, benzthiazolyl-2-amine, benzoxazolyl-2-amine, 1,3,4-triazolyl-2-amine, 1-thia-3,4-diazolyl-2-amine, benzimidazolyl-2-amine and the methoxy, ethoxy, phenyl, chlorine, bromine, methyl, ethyl, carbomethoxy and carboethoxy derivatives thereof, α-and β-tetrahydrofurfurylamine, 2-furfurylamine, N-α- and N-β-tetrahydrofurfuryl-N-methylamine, thiophenyl-2-amine and pyridyl-3-amine.

The reaction with the amines is preferably carried out in solvents, such as hydrocarbons, ethers, dioxane, chlorinated hydrocarbons etc, at elevated temperature (for example 30° to 200° C).

The saponification of the cyano group in 3-position, which is effected until decarboxylation occurs, is performed either with strong alkalies, such as sodium hydroxide solution or potassium hydroxide solution, or preferably with strong acids, such as phosphoric acid or, in particular, concentrated sulphuric acid, at temperatures of 30° to 180° C, preferably however from 100° to 150° C.

Preferred embodiments are the 5-nitropyridines which do not contain any sulphonic acid groups, for example 5-nitropyridines in which preferably $R_5$ and $R_6$ are aliphatic groups, and, in particular, 5-nitropyridines in which in 2-position the radicals $R_5$ and $R_6$, together with the nitrogen atom to which they are attached, form a ring, i.e. they are for example part of a morpholino, pyrrolidino, piperidino or piperazino group.

Preferred 5-nitropyridines are also those in which $R_1$, $R_2$, $R_3$ and $R_4$ are hydrogen atoms.

Aryl, aralkyl, cycloalkyl and aliphatic groups are to be understood as meaning preferably groups of the benzene series, benzyl, phenethyl, cyclohexyl or alkyl groups containing at most 12 carbon atoms, it being possible for these last mentioned groups to contain oxygen or sulphur atoms or imino groups. The radicals R located at the same nitrogen atom can, as stated, be attached to each other directly or through heteroatoms, in particular oxygen and sulphur atoms, to form 5- or 6-membered rings.

Suitable examples of the radicals $R_1$, $R_2$, $R_3$, $R_4$, $R_5$ and $R_6$ are hydrogen atoms or alkyl groups of 1 to 10 carbon atoms, for example, methyl, ethyl, propyl, isopropyl, butyl, sec.butyl, n-pentyl, hexyl, allyl, β-ethylhexyl and octyl groups, which can contain oxygen atoms and be substituted by hydroxyl, carboxyl, $C_2$-$C_{10}$-carbalkoxy, $C_1$-$C_8$-alkoxy, phenoxy, pyrrolidonyl, $C_1$-$C_{10}$-acyloxy, phenyl groups which are optionally substituted by halogen atoms (preferably by chlorine or bromine atoms), lower alkyl or lower alkoxy, β-hydroxyethyl, cyano, $C_1$-$C_5$-alkanoylamino or lower carboalkoxy groups, or by benzyl or phenethyl or cycloalkyl groups, or are linked together to form a piperidine, pyrrolidine, morpholine, piperazine or methylpiperazine ring.

Suitable acyl groups are for example fatty acid radicals containing not more than 10 carbon atoms, such as formyl, acetyl, propionyl, butyryl groups; alkylcarbonyl groups of not more than 5 carbon atoms, such as methylaminocarbonyl, ethylaminocarbonyl, propylaminocarbonyl or butylaminocarbonyl groups; alkyloxycarbonyl groups of not more than 5 carbon atoms, such as methoxycarbonyl, ethoxycarbonyl, propoxycarbonyl, or butoxycarbonyl groups, phenylcarbamyl or phenoxycarbonyl groups, benzoyl, phenoxyacetyl, chloroacetyl or phenylacetyl groups.

Suitable groups which contain hydroxyl groups are for example: β-hydroxyethyl or β-hydroxypropyl, γ-hydroxypropyl, β,γ-dihydroxypropyl,ω-hydroxyhexyl, and the radicals of the formulae

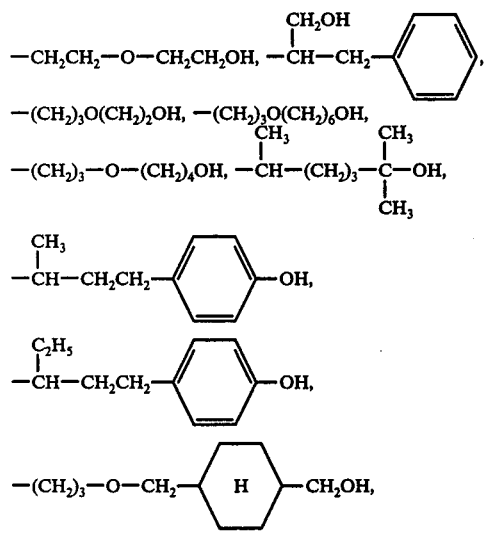

the alkoxyalkyl groups, β-methoxyethyl, γ-methoxypropyl, γ-iso-propoxypropyl, γ-butoxypropyl, β-ethoxyethyl, γ-ethoxypropyl, and the groups of the formulae

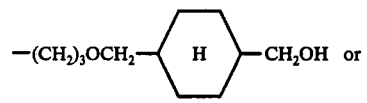

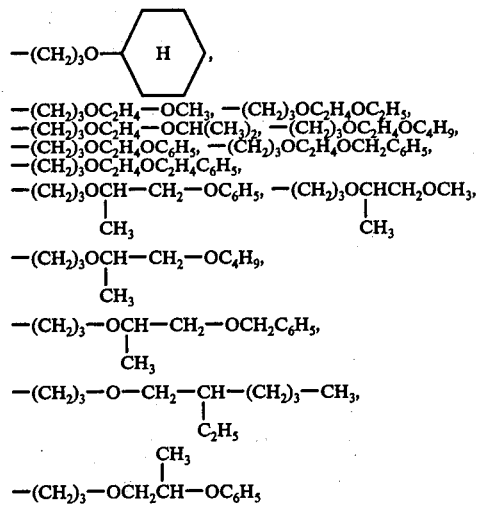

and the corresponding compounds in which the grouping

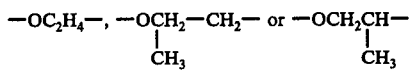

is present twice, three or four times, and compounds in which $C_6H_5$ is replaced by $C_6H_4CH_3$.

Mention is also to be made of:

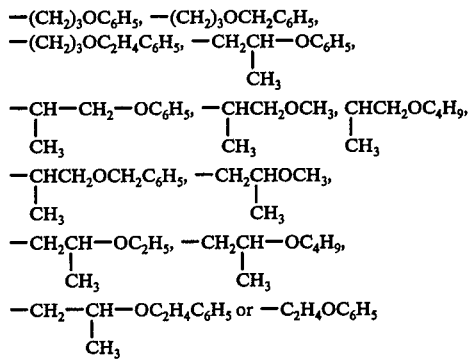

and the groups with —$C_6H_4CH_3$ in place of $C_6H_5$.

The carboxalkyl and carbalkoxyalkyl groups of the formulae:

$CH_2$—COOY, $CH_2$—$CH_2$—COOY,
$(CH_2)_5$—COOY or
$(CH_2)_2$—O—CO—$(CH_2)_2$—COOY, wherein Y represents for example a hydrogen atom, a methyl, ethyl, propyl, benzyl, β-hydroxyethyl, ω-hydroxyhexyl, γ-hydroxybutyl, β-methoxyethyl, γ-methoxypropyl, γ-ethoxypropyl, β-phenoxyethyl or β-hydroxyethoxyethyl group, a group of the formula

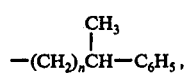

wherein n is 1 or 2, the acyloxyalkyl groups of the formulae

—CH$_2$—CH$_2$—O—acyl, —(CH$_2$)$_3$—O—acyl,

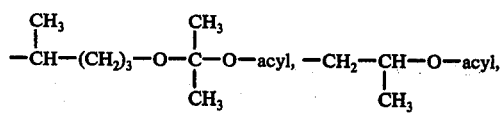

—(CH$_2$)$_6$—O—acyl,
—(CH$_2$)$_2$—O—(CH$_2$)$_2$—O—acyl or
—(CH$_2$)$_3$—O—(CH$_2$)$_4$—O—acyl, wherein the term "acyl" represents one of the acyl groups listed hereinafter, but especially a group of the formulae

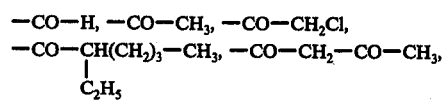

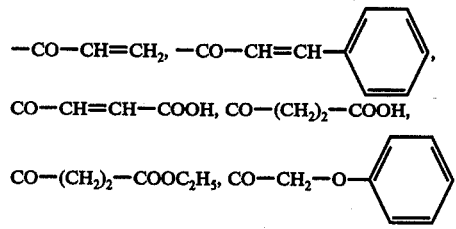

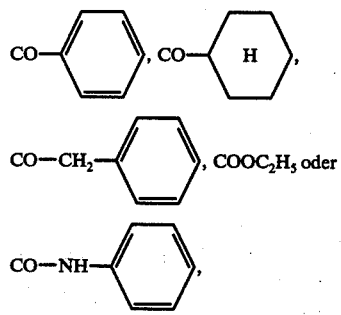

the pyrrolidonylalkyl groups of the formulae:

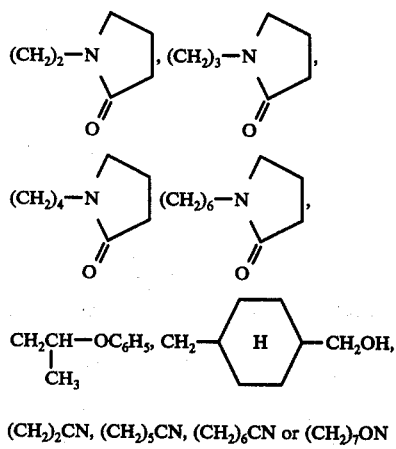

(CH$_2$)$_2$CN, (CH$_2$)$_5$CN, (CH$_2$)$_6$CN or (CH$_2$)$_7$ON substituted or unsubstituted cycloalkyl and polycycloalkyl groups:

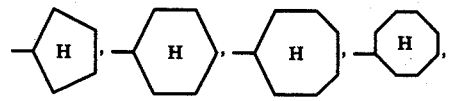

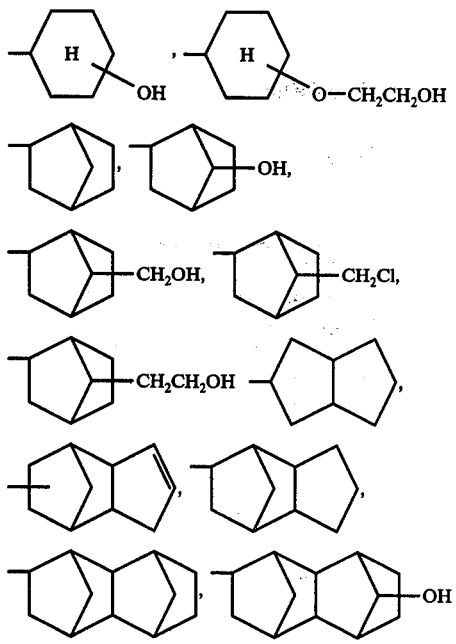

Aralkyl groups of the formulae:

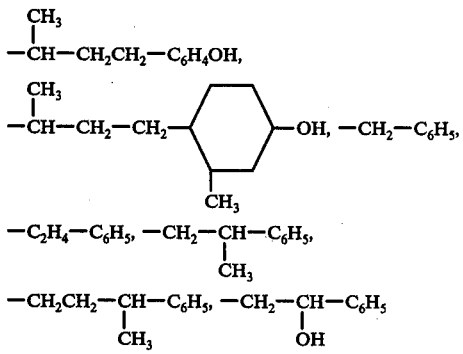

and the corresponding toluene derivatives.

Substituted or unsubstituted phenyl groups of the formulae:

C$_6$H$_5$, C$_6$H$_4$Cl, C$_6$H$_3$Cl$_2$, C$_6$Cl$_4$CH$_3$, C$_6$H$_3$(CH$_3$)$_2$,
C$_6$H$_4$CN, C$_6$H$_4$OCH$_3$, C$_6$H$_4$OC$_2$H$_5$ and
C$_6$H$_4$NHCOCH$_3$, C$_6$H$_4$—OH and
C$_6$H$_4$—O—C$_2$H$_4$—OH.

In a particular embodiment of the invention, cyanotriaminopyridines are used as starting materials in which at least one R of the substituents R$_1$, R$_2$, R$_3$, R$_4$, R$_5$ and R$_6$, preferably of R$_2$, R$_4$ or R$_5$, is a group of the formula

—R$_6'$—A, wherein R$_6'$ is an aliphatic, cycloaliphatic, araliphatic or aromatic group and A represents an acid group, such as —SO$_3$H, —PO$_3$H$_2$ and COOH.

Examples of groups R$_1$, R$_2$, R$_3$, R$_4$, R$_5$ and R$_6$ which contain sulphonic acid groups are:

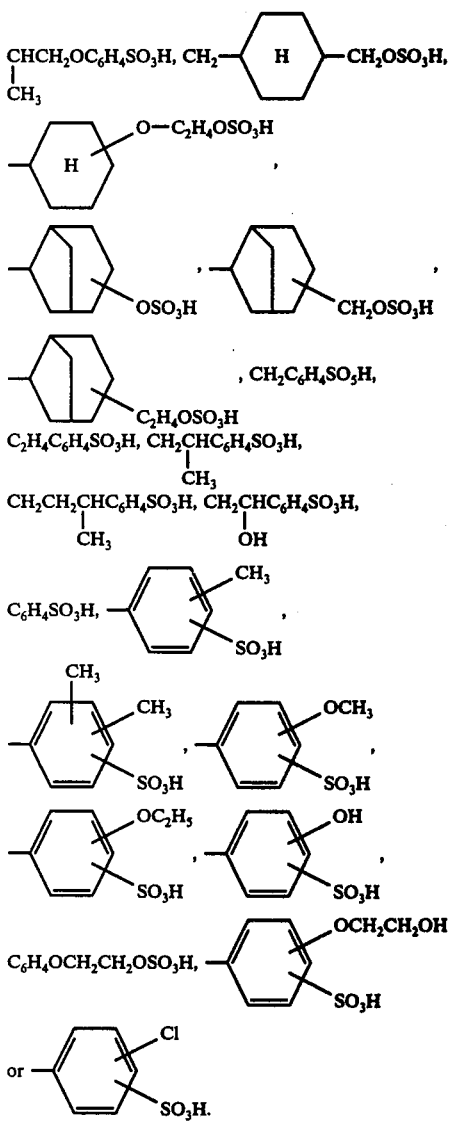

A further embodiment of the invention comprises 5-nitropyridines which do not contain acid groups and $R_1$, $R_2$, $R_3$, $R_4$, $R_5$ and $R_6$ together contain at least one or more basic, optionally cationic groups, namely in particular those wherein at least one R of $R_2$, $R_4$ and $R_5$ is a group of the formula $$-R_5'-Q,$$

wherein $R_5'$ is a divalent aliphatic, cycloaliphatic, araliphatic or aromatic group and Q is respectively an optionally quaternised amino, hydrazino, etherified hydroxylamino or pyridine group which is bound direct or through a bridge.

Suitable contenders for the group $R_5'$ are substituted or unsubstituted alkylene and phenylene groups, for example

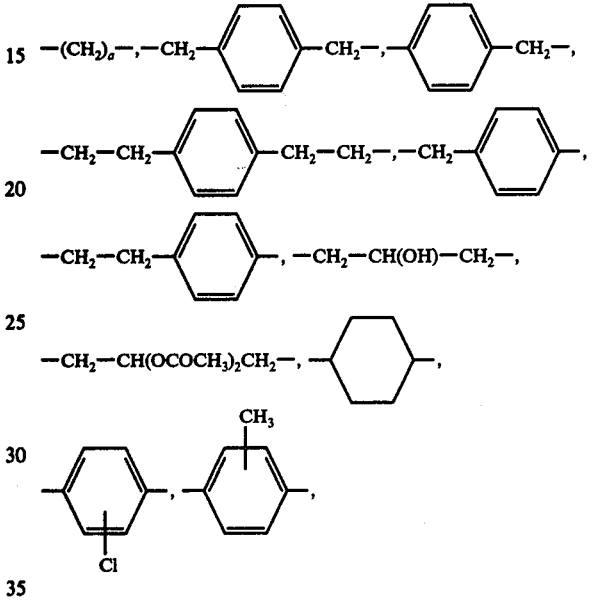

wherein $a$ is an integer from 1 to 12.

The basic group Q together with $R_5$ and $NR_6$ can also form a 5- or 6-membered ring.

Suitable groups $R_1$, $R_2$, $R_3$, $R_4$, $R_5$ and $R_6$ with basic unquaternised or quaternised nitrogen atoms are:

$$-(CH_2)_a-N \text{ (lower alkyl)}_2$$

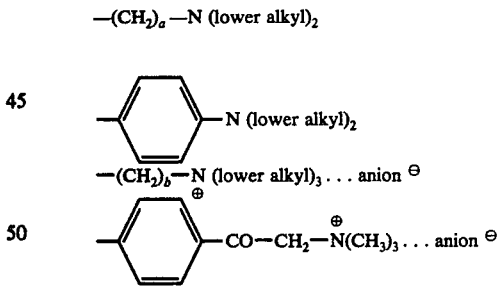

wherein the term "lower" qualifying alkyl, alkoxy, carbalkoxy etc., denotes that the alkyl group in question contains 5, preferably only 4, carbon atoms.

Examples of suitable basic groups Q are those of the formula

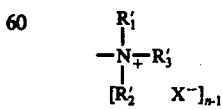

wherein $R_1'$ and $R_2'$ represent a hydrogen atom or an alkyl group, in particular a $C_1$-$C_4$-alkyl group, an aralkyl group, in particular a benzyl or cycloalkyl group, in particular a cyclohexyl group, $R_3'$ represents a hydrogen atom or an alkyl, aralkyl, cycloalkyl or alkoxy group or an amino group, and wherein the nitrogen atom together with $R_1'$ and/or $R_2'$ and/or $R_3'$ can form part of a heterocyclic ring. X is an anion and n is 1 or 2. The anions can be those of strong inorganic and organic acids, for example chloride, bromide, iodide, nitrate, sulphate, in particular hydrogen sulphate and phosphate, arylsulphonates and alkylsulphonates (in particular benzenesulphonate and the derivatives thereof which are substituted by nitro, chlorine, bromine, $C_1$-$C_4$-alkyl and $C_1$-$C_4$-alkoxy groups, and $C_1$-$C_4$-alkylsulphonates). Further suitable anions are the hemiesters of alkylsulphuric acid containing 1 to 4 carbon atoms and the double salts of zinc and cadmium halides.

Examples of such anions are: benzenesulphonate, p-toluenesulphonate, p-methoxybenzenesulphonate, methanesulphonate, ethanesulphonate, formiate, acetate, chloroacetate, propionate, lactate, tartrate, benzoate, methyl benzoate, methylsulphate, ethylsulphate, $ZnCl_3$—, $CdCl_3$—, carbonate and bicarbonate.

The nitro-amino-pyridines of the present invention are useful coupling components for obtaining dyes, for example dyes of the disperse series. These compounds are used in known manner for such coupling reactions.

Further fields of use for the nitroaminopyridines of the present invention and the products which can be obtained therefrom are medicaments, agrochemicals, such as insecticides and also bactericides.

In the following illustrative but non-limitative Examples the parts and percentages are by weight, unless otherwise indicated. The relationship between parts by weight and parts by volume is the same as that between the gram and the cubic centimetre.

EXAMPLE 1

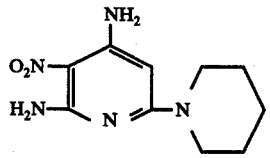

(a) 183 Parts of $H_2SO_4$ (concentrated) are charged into a reaction vessel and, with stirring, 40 parts of 2-piperidino-3-cyano-4,6-diamino-pyridine are added by small amounts whilst the temperature is kept at 15° to 20° C by cooling with ice. After the starting material has completely dissolved, the solution is cooled to 10° to 15° C, and at this temperature 25.8 parts of nitrosulphuric acid (50%) are added dropwise in the course of 20 to 30 minutes. When the addition is complete, the mixture is stirred for 3 hours at room temperature. The solution is poured onto 150 parts of ice, so that the temperature does not exceed 20°-25° C, and then neutralised with concentrated sodium hydroxide solution while cooling externally at room temperature. The precipitated brown product is collected by filtration, washed free of salt with 500 parts of $H_2O$ and dried at 70° C in vacuo.

(b) 460 Parts of sulphuric acid (85 to 90% by volume) are charged into a reaction vessel and 36 parts of the nitro product are added by small amounts with stirring. The solution is stirred for 4 hours at 100° C (internal temperature), cooled, and poured onto 300 parts of ice, so that the temperature does not exceed 20°-25° C. The solution is neutralised with concentrated sodium hydroxide solution while cooling. The brownish-black product is collected by filtration, washed free of salt with 300 parts of $H_2O$ and dried in vacuo at 70° C.

Recrystallisation from chloroform yielded a yellow product of the formula

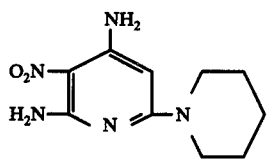

with a melting point of 132°-135° C.

EXAMPLE 2

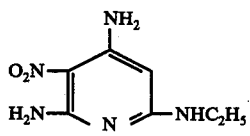

36.6 Parts of concentrated sulphuric acid are charged into a reaction vessel and 20 parts of 2-ethylamino-3-cyano-4,6-diamino-pyridine are added by small amounts with stirring, whilst the temperature is kept at 15° to 20° C by cooling with ice. After the starting material has completely dissolved, the solution is cooled to 10°-15° C and at this temperature 15.7 parts of nitrosulphuric acid (50%) are added dropwise. When the addition is complete, the reaction solution is stirred for 3 hours at room temperature. The solution is poured onto 100 parts of ice, so that the temperature does not exceed 20°-25° C. With cooling, the solution is adjusted to pH 2 with concentrated NaOH, whereupon the yellowish brown hydrosulphate of the product precipitates. This precipitate is sollected by filtration and washed with 200 parts of ice-water. The product is dried at 70° in vacuo.

Neutralisation of a sample, extraction with chloroform and concentration of the extract yielded a yellow product with a melting point of 153°-157° C.

180 Parts of sulphuric acid (85-90% by volume) are charged into a reaction vessel and 18 parts of the nitro product are added by small amounts with stirring. The solution is stirred for 3 hours at 110° C (internal temperature), allowed to cool and poured onto 150 parts of ice, so that the temperature does not exceed 20°-25° C. The solution is adjusted to a pH of 2 with concentrated sodium hydroxide solution while cooling. The precipitated yellowish-brown hydrosulphate of the product is collected by filtration, washed with 200 parts of ice-water and dried at 70° C in vacuo. The free base, which is recrystallised from chloroform/petroleum ether, has a melting point of 122°-125° C. It has the formula

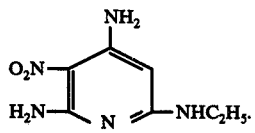

EXAMPLE 3

Synthesis of 2-bromo-3-cyano-4,6-diamino-5-nitro-pyridine

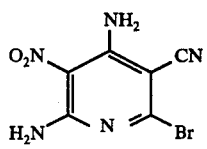

460 Parts of concentrated $H_2SO_4$ are charged into a reaction vessel and 106.5 parts of 2-bromo-3-cyano-4,6-diamino-pyridine are added by small amounts whilst the temperature is kept at 15°–20° C by cooling with ice. After the starting material has dissolved completely, the solution is cooled to 10° to 15° C and at this temperature 69.1 g of nitrosulphuric acid (50%) are added dropwise in the course of 45 minutes. When the addition is complete, the reaction solution is stirred for 1½ hours at room temperature, then poured onto 500 parts of ice so that the temperature does not exceed 20°–25° C (ice bath). The suspension is neutralised with 1000 parts of concentrated NaOH while cooling, whereupon the product precipitates completely. The brown product is filtered off, washed free of salt with 1500 parts of water and dried in vacuo at 70° C.

EXAMPLE 4

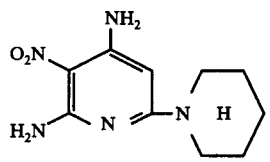

10.95 Parts of 2-bromo-3-cyano-4,6-diamino-nitropyridine are suspended in 44 parts of chlorobenzene and reacted with 3.69 parts of piperidine for 2 hours at 90° C. The reaction mixture is stirred overnight at room temperature and the chlorobenzene is removed by steam distillation. The aqueous suspension is filtered, washed with 200 parts of water and the product is dried at 70° C in vacuo.

Decarboxylation is effected by dissolving 8.6 parts of the above product in 54 parts of $H_2SO_4$ (85–90% by volume) and reacting it for 1½ hours at 110° C. After it has been cooled to room temperature, the solution is poured onto 50 parts of ice, so that the temperature does not exceed 20°–25° C (ice bath) and neutralised with 105 parts of concentrated NaOH while cooling. The precipitated product is collected by filtration, washed free of salt with 500 parts of water and dried in vacuo at 70° C.

The aminopyridines of the formula

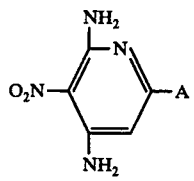

listed in the following table are obtained in analogous manner by using the amines A–H.

| No. | A |
|---|---|
| 1 | $NHCH_2CH_2OH$ |
| 2 | $NHCH_2CH_2-O-CH_2CH_2-OH$ |
| 3 | NH—CH(CH₃)—CH₂—C(CH₃)₂—OH |
| 4 | $NH-CH_2CH_2OCH_3$ |
| 5 | $NHCH_2CH_2OC_6H_5$ |
| 6 | NH—CH₂CH₂O—C₆H₁₁ |
| 7 | $NH(CH_2)_3OCH_2H_4-O-CH_3$ |
| 8 | $NH-CH_2-CH(CH_3)-O-CH_3$ |
| 9 | $N(CH_2CH_2OH)_2$ |
| 10 | $N(CH_2CH_2OCH_3)_2$ |
| 11 | N(CH₂CH₂—OH)(CH—CH₂OC₆H₅) |
| 12 | $NH-C_6H_5$ |
| 13 | $NH-CH_2-C_6H_5$ |
| 14 | $NH-C_6H_{11}$ |
| 15 | $NH-CH_2C(=O)-OH$ |
| 16 | $NH_2-CH_2-CH_2-N$ (2-oxopiperidinyl) |
| 17 | NH—(tricyclic)—OH |
| 18 | $NH-C_6H_4Cl$ |
| 19 | $NHC_6H_4-CH_3$ |
| 20 | $NHC_6H_4-OH$ |
| 21 | $NHCH_2-CH_2-SO_3H$ |
| 22 | $NH-C_6H_4-SO_3H$ |
| 23 | $NH-C_6H_4N(CH_3)_2$ |
| 24 | $NHCH_2CO-CH_2-\overset{\oplus}{N}-(CH_3)_3 \ HSO_4^{\ominus}$ |

| No. | A |
|---|---|
| 25 | 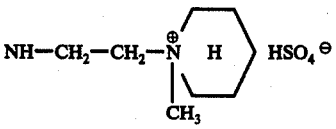 |

EXAMPLE 5

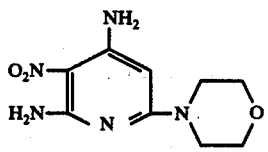

15.5 Parts of 2-bromo-3-cyano-4,6-diamino-5-nitropyridine are suspended in 77 parts of chlorobenzene and reacted with 6.5 parts of morpholine for 2 hours at 90° C. The reaction mixture is stirred overnight at room temperature and the chlorobenzene is removed by steam distillation. The brown product is filtered off, washed with 60 parts of water and dried in vacuo at 70° C.

The decarboxylation is effected by dissolving 10 parts of the product in 90 parts of $H_2SO_4$ (85 to 90% by volume) and reacting it for 1 hour at 110° C. The reaction solution is cooled to room temperature and then poured onto 50 parts of ice, so that the temperature does not exceed 20°–25° C (ice bath) and neutralised with 160 parts of concentrated NaOH while cooling. The precipitated brown product is filtered off, washed free of salt with 600 parts of water and dried in vacuo at 70° C.

EXAMPLE 6

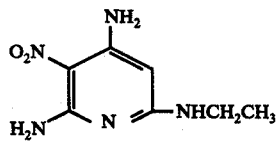

10.4 Parts of 2-bromo-3-cyano-4,6-diamino-5-nitropyridine are reacted with 13 parts of 70% ethylamine and 10 parts of ethanol for 4 hours in a bomb tube. The reaction solution is evaporated to dryness and the residue is suspended in 20 parts of water. The product is filtered off, washed with 20 parts of ethanol and dried in 70° C in vacuo.

The decarboxylation is effected by dissolving 4.8 parts of the above product in 36 parts of $H_2SO_4$ (85 to 90% by volume) and reacting it for 1 hour at 110° C. The reaction solution is cooled to room temperature and then poured onto 50 parts of ice, so that the temperature does not exceed 20°–25° C (ice bath), and neutralised with 70 parts of concentrated NaOH while cooling. The precipitated brown product is filtered off, washed free of salt with 100 parts of water and dried at 70° C in vacuo.

EXAMPLE 7

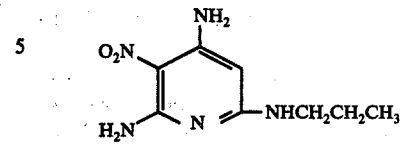

9.2 Parts of 2-bromo-3-cyano-4,6-diamino-5-nitropyridine are reacted with 10.6 parts of propylamine and 10 parts of ethanol for 4 hours in a bomb tube at 100° C. The reaction solution is evaporated to dryness and the residue is suspended in 20 parts of water. After filtration, the product is washed with 20 parts of ethanol and dried at 70° C in vacuo. Decarboxylation is effected by dissolving 5 parts of the product in 36 parts of $H_2SO_4$ (85–90% percent by volume) and reacting it for 1½ hours at 110° C. The solution is cooled to room temperature and then poured onto 50 parts of ice, so that the temperature does not exceed 20°–25° C (ice bath), and neutralised with 70 parts of concentrated NaOH while cooling. The resinous residue is filtered off and dried in vacuo at 60° C, when it solidifies.

EXAMPLE 8

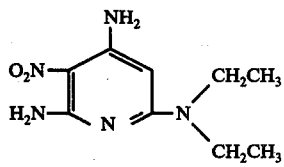

15 Parts of 2-bromo-3-cyano-4,6-diamino-5-nitropyridine are suspended in 33 parts of chlorobenzene and reacted with 5.3 parts of diethylamine for 4 hours at 50° C. After the reaction mixture has been stirred overnight at room temperature, the chlorobenzene is removed by steam distillation, the brown product filtered off, washed with 200 parts of water and dried at 60° to vacuo.

Decarboxylation is effected by dissolving 9 parts of the product in 63 parts of $H_2SO_4$ (85–90% by volume) and reacting it for 1½ hours at 110° C. The solution is cooled to room temperature and then poured onto 40 parts of ice, so that the temperature does not exceed 20°–25° C (ice bath), and neutralised with 115 parts of concentrated NaOH. The precipitated product is filtered off, washed free of salt with 700 parts of water and dried at 70° C in vacuo.

EXAMPLE 9

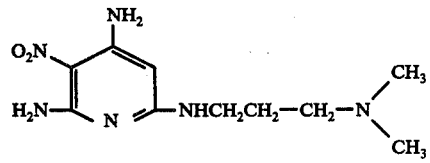

20.64 Parts of 2-bromo-3-cyano-4,6-diamino-5-nitropyridine are suspended in 50 parts of ethanol and reacted with 16.3 parts of 3-dimethylamino-1-propylamine for 2½ hours at 70°–75° C. After cooling to room temperature, the product is filtered off, washed with 100 parts of ethanol and dried at 70° C in vacuo.

Decarboxylation is effected by dissolving 12 parts of the product in 54 parts of $H_2SO_4$ (85–90% by volume) and reacting it for 2 hours at 110° C. The solution is cooled to room temperature and then poured onto 30 parts of ice, so that the temperature does not exceed 20°–25° C (ice bath), and adjusted to pH 9 with 100 parts of concenctrated NaOH while cooling. The aqueous solution, which contains the partially precipitated product and sodium sulphate, is extracted with a total amount of 1500 parts of ethyl acetate. The ethyl acetate phase is dried over calcined $Na_2SO_4$ and evaporated to dryness. The resinous product is dried at 60° C in vacuo, when it solidifies.

We claim:

1. A process for the manufacture of 2,4,6-triamino-5-nitro-pyridines of the general formula

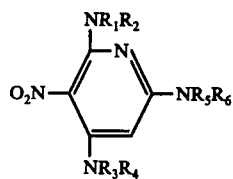

wherein $R_1$, $R_2$, $R_3$, $R_4$, $R_5$ and $R_6$ independently represents hydrogen;

alkyl of 1 to 10 carbon atoms which are unsubstituted or substituted by hydroxy, carboxy, $C_2$-$C_{10}$ carbalkoxy, $C_1$-$C_8$-alkoxy, phenoxy, pyrrolidonyl or $C_1$-$C_{10}$ acyloxy;

phenyl which is unsubstituted or substituted by halo, lower alkyl, lower alkoxy, β-hydroxyethyl, cyano, $C_1$-$C_5$ alkanoylamino or lower carboalkoxy;

benzyl;

phenethyl;

cycloalkyl;

a group of the formula $CH_2CH_2SO_3H$, $CH_2CH_2OSO_3H$, $(CH_2)_3OSO_3H$,

$(CH_2)_4OSO_3H$, $(CH_2)_6OSO_3H$,

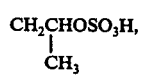

$(CH_2)_2O(CH_2)_2OSO_3H$, $(CH_2)_3O(CH_2)_2OSO_3H$,
$(CH_2)_3O(CH_2)_4OSO_3H$,
$(CH_2)_3OC_2H_4OCH_2C_6H_4SO_3H$,
$(CH_2)_3OC_2H_4OC_2H_4C_6H_4SO_3H$,
$(CH_2)_3OC_2H_4OC_6H_4SO_3H$, $CH_2CH_2OC_6H_4SO_3H$,
$(CH_2)_3OC_6H_4SO_3H$, $(CH_2)_3OCH_2C_6H_4SO_3H$, $(CH_2)_3OC_2H_4C_6H_4SO_3H$, 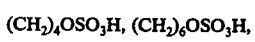

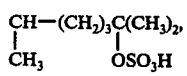

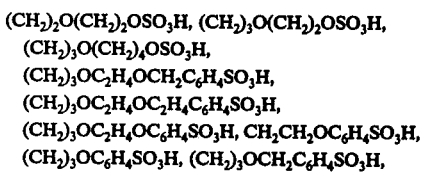

$CH_2C_6H_4SO_3H$, $C_2H_4C_6H_4SO_3H$, 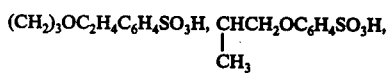

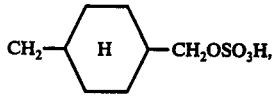, $C_6H_4SO_3H$,

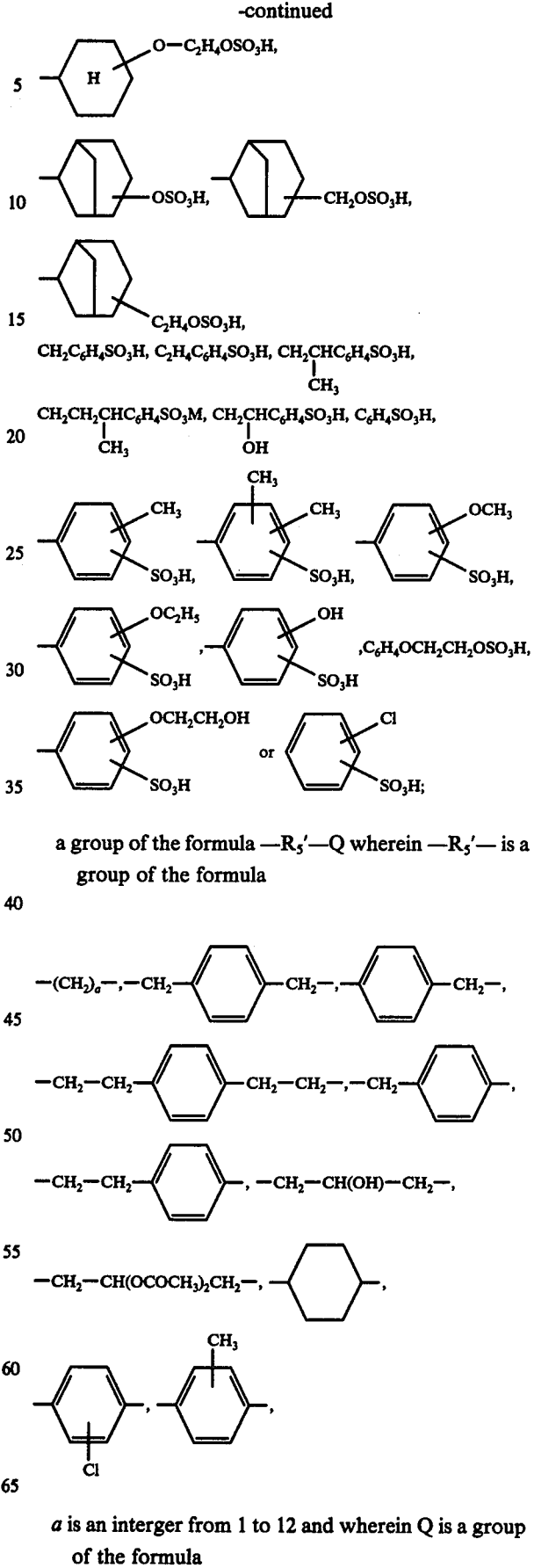

a group of the formula —$R_5'$—Q wherein —$R_5'$— is a group of the formula a is an interger from 1 to 12 and wherein Q is a group of the formula

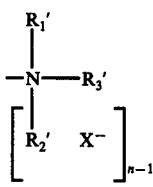

where
- $R_1'$ and $R_2'$ are hydrogen, $C_1-C_4$ alkyl, benzyl or cyclohexyl,
- $R_3'$ is hydrogen, $C_1-C_4$ alkyl, benzyl, cyclohexyl, alkoxy or amino; or
- $R_1'$, $R_2'$ and $R_3'$ are, together with the nitrogen to which they are attached, pyridyl,
- $n$ is 1 or 2, and
- the anion $X^-$ is chloride, bromide, iodide, nitrate, hydrogen sulphate, phosphate, benzenesulphonate, (nitro, chloro, bromo, $C_1-C_4$-alkyl or $C_1-C_4$-alkoxy)-benzenesulphonate, $C_1-C_4$ alkylsulphonate, or $C_1-C_4$ alkylsulphate; or the double salt thereof with zinc or cadmium halide; or
- $R_1$ and $R_2$, $R_3$ and $R_4$ or $R_5$ and $R_6$ together with the nitrogen to which they are attached independently represent pyrrolidino, piperidino, piperazino, N-lower alkylpiperazino, (N-formyl- or N-lower alkylcarbonyl)-piperazino or morpholino;

which process comprises
nitrating the corresponding 2-bromo-3-cyano-4,6-diamino pyridine with a mixture of nitric acid and sulphuric acid at $-20°$ to $+40°$ C to form the corresponding 2-bromo-3-cyano-4,6-diamino-5-nitro pyridine,
aminating said 2-bromo-3-cyano-4,6-diamino-5-nitro pyridine with an amine of the formula $HNR_5R_6$ at a temperature of 30° to 200° C to form the corresponding 3-cyano-2,4,6-triamino-5-nitro pyridine,
and saponifying the resultant 3-cyano-2,4,6-triamino-5-nitro pyridine with concentrated sulphuric acid at a temperature of 90° to 150° C until decarboxylation is effected.

2. A process according to claim 1, wherein the nitration is carried out at $-10°$ to $+20°$ C.

3. A process according to claim 1, wherein the decarboxylation is effected at 100° to 120° C.

4. A process according to claim 1, wherein triamino-5-nitro-pyridines are manufactured, in which $R_1$, $R_2$, $R_3$, $R_4$, $R_5$ and $R_6$ contain no acid or basic groups.

5. A process according to claim 1, wherein a start is made from 3-cyanopyridines in which at least one R represents a group of the formula $-R_5'-Q$.

6. A process according to claim 5, wherein a start is made from 3-cyanopyridines in which Q represents a group of the formula

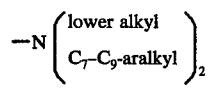

7. A process according to claim 5, wherein a start is made from 3-cyanopyridines in which Q represents a group of the formula

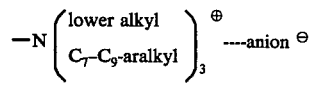

8. A process according to claim 1, wherein one of the pairs $R_1$ and $R_2$, $R_3$ and $R_4$, $R_5$ and $R_6$, together with the nitrogen atom to which it is attached, forms a piperidine, piperazine, morpholine or pyrrolidine system.

* * * * *